United States Patent
Zhu et al.

(10) Patent No.: US 9,161,930 B2
(45) Date of Patent: Oct. 20, 2015

(54) PHARMACEUTICAL COMPOSITION FOR DIABETIC NEPHROPATHY AND ITS PREPARATION AND APPLICATION

(75) Inventors: Quan Zhu, Guangzhou (CN); Xinghua Shi, Guangzhou (CN); Dan Tang, Guangzhou (CN); Zhaoguang Zheng, Guangzhou (CN); Bao He, Guangzhou (CN); Tingting Duan, Guangzhou (CN); Fei Gu, Guangzhou (CN); Huiquan Cheng, Guangzhou (CN); Xiaoling Huang, Guangzhou (CN); Yanxia Huang, Guangzhou (CN); Rushang Wang, Guangzhou (CN)

(73) Assignee: Guangzhou Consun Medicine R & D Co., Ltd., Guangzhou (CN)

( * ) Notice: Subject to any disclaimer, the term of this patent is extended or adjusted under 35 U.S.C. 154(b) by 367 days.

(21) Appl. No.: 13/287,624

(22) Filed: Nov. 2, 2011

(65) Prior Publication Data

US 2012/0053236 A1  Mar. 1, 2012

Related U.S. Application Data

(60) Division of application No. 12/823,357, filed on Jun. 25, 2010, now abandoned, which is a continuation of application No. PCT/CN2009/000351, filed on Apr. 1, 2009.

(30) Foreign Application Priority Data

Jan. 16, 2009  (CN) .......................... 2009 1 0036716

(51) Int. Cl.
| | |
|---|---|
| *A61K 31/27* | (2006.01) |
| *A61K 9/00* | (2006.01) |
| *A61K 9/20* | (2006.01) |
| *A61K 9/48* | (2006.01) |

(52) U.S. Cl.
CPC .............. *A61K 31/27* (2013.01); *A61K 9/0056* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 9/4875* (2013.01)

(58) Field of Classification Search
CPC ....... A61K 31/27; A61K 9/2054; A61K 9/48; A61K 9/2059; A61K 9/4875
USPC ................................... 514/478; 424/464, 465
See application file for complete search history.

(56) References Cited

U.S. PATENT DOCUMENTS 3,934,006 A * 1/1976 Frommer et al. ............. 424/115

FOREIGN PATENT DOCUMENTS

| CN | 101129602 | * | 2/2008 |
|---|---|---|---|
| KR | 2006/080828 | * | 8/2006 |

OTHER PUBLICATIONS

Ma ST et al., Znongguo Ying Yong Sheng Li Xue Za Zhi, May 2008;24(2):201-4.*
Chi DM et al. "Tubulin-dependent hydrolysis of guanosine triphosphate as a screening test to identify new antitubulin compounds with potential as antimitotic agents: application to carbamates of aromatic amines." Cancer Res. Mar. 15, 1989;49(6):1344-8.
Nam SY. et al. "Cortex mori extract induces cancer cell apoptosis through inhibition of microtubule assembly." Arch Pharm Res. Apr. 2002;25(2):191-6.
Nasar M. et al. "Computer-assisted structure—anticancer activity correlations of carbamates and thiocarbamates." J Pharm Sci. Aug. 1985;74(8):831-6.

* cited by examiner

*Primary Examiner* — Shobha Kantamneni
(74) *Attorney, Agent, or Firm* — Locke Lord LLP; Gabriel J. McCool

(57) ABSTRACT

The invention relates to application of 4,4'-diphenylmethane-bis(methyl) carbamates (DPMC) extracted and isolated from Cortex Mori and preparation of medicine for diabetic nephropathy. The pharmaceutical composition is made up of DPMC as active ingredient and the normal drug carriers, and the weight percentage of active ingredient is 0.1-99.5%. For the remarkable effect of prevention and cure for diabetic nephropathy and convenience for use, it will be a new facultative drug for patients.

2 Claims, 1 Drawing Sheet

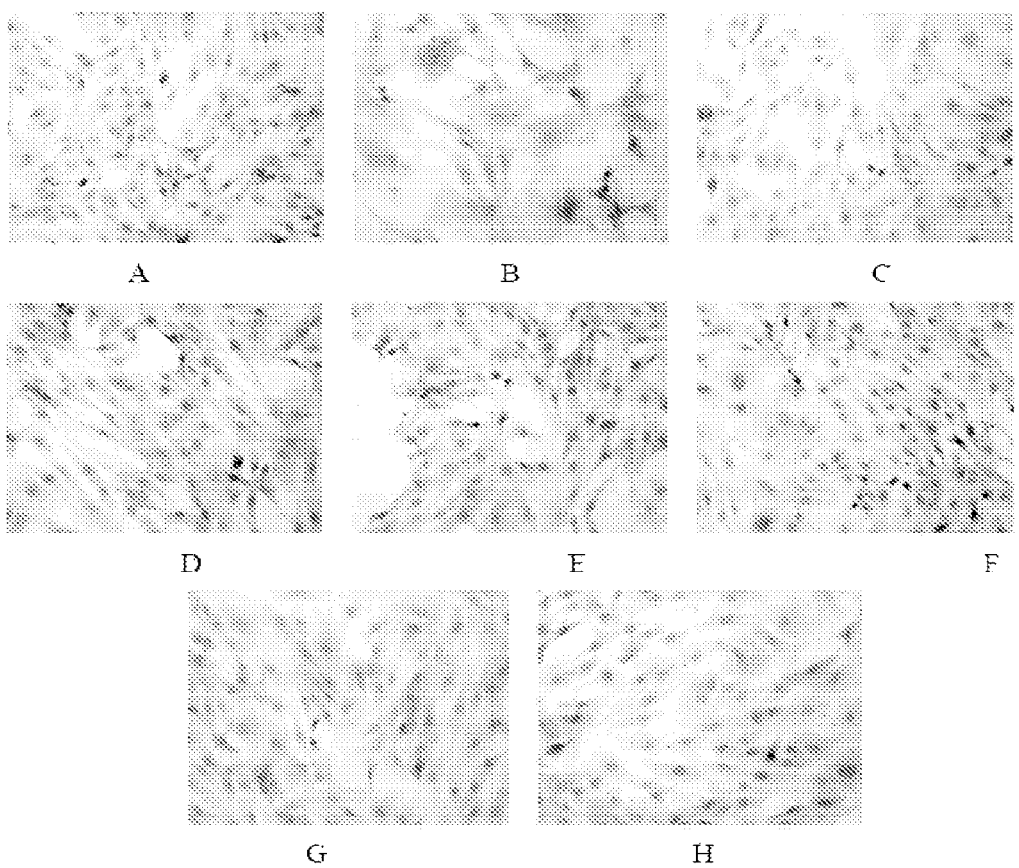

PHARMACEUTICAL COMPOSITION FOR DIABETIC NEPHROPATHY AND ITS PREPARATION AND APPLICATION

RELATED APPLICATIONS

This application is a divisional application of U.S. application Ser. No. 12/823,357, filed on Jun. 25, 2010 now abandoned, which is a continuation of PCT/CN2009/000351, filed on Apr. 1, 2009, which claims priority to China Patent Application No.: CN200910036716.6, filed on Jan. 16, 2009. The entire contents of the aforementioned patent applications are hereby incorporated herein by reference in their entirety.

FIELD OF THE INVENTION

The present invention relates to the field on preparation of traditional Chinese medicine, in particular to the preparation of a pharmaceutical composition whose active ingredient is 4,4'-diphenylmethane-bis(methyl) carbamates (DPMC) for diabetic nephropathy and its application.

BACKGROUND OF THE INVENTION

Diabetes mellitus and its chronic complications have seriously affected the healthy and life quality of human being. The number of patient has increased in recent years and the attack rate of diabetic nephropathy in every age group is 2.8% in 2000 when in 2030 is predicted to be 4.4% all around the world, which means that the number of diabetic patient will increase from 1.71 hundred millions in 2000 to 3.33 hundred million in 2030. With the increasing attack rate every year, the quantities of patients in China has been second only India. Therefore, the prevention and cure of diabetic and its complications has been a very important topic these days. Diabetic nephropathy (DN), one of the important complications of diabetic, has been the first place of diseases which leads to the final stage of renal failure. As shown by the data of world health organization that about 30% of I type and 25%-40% II type diabetic patients would improve to be DN patients if the blood glucose was not controlled. Because of delitescence and difficult to discover of DN in earlier period, it will can not be reverse when the symptom of renal affection appears. The yearlong diabetic can destroy filtration function of renal and express as microamount albuminuria. With the extend of disease course, albuminuria will increase and the ability of renal for eliminating toxin in blood decays gradually, which leads to the end stage renal disease (ESRD) and the patients can only maintain their life by hematodialysis or kidney transplant. Thereby, it is badly need to deeply elucidate the mechanism of DN, rich and consummate the measures of prevention and cure.

Advanced glycation end products (AGES) is a covalence conjugate of macromolecule and glyc-carbonyl without catalysis of enzyme. Under the condition of catalysis of non-enzyme, firstly the reversible Schiffs base is formed by free aldehyde of amylaccum molecule and amino group of protein, secondary stationary ketoamine compounds (Amadori products) are formed by the structural rearrangement of Schiffs base, then the stationary and nonreversible AGEs are formed after the reactions of dehydration, oxidation and condensation. AGEs relates closely to the complication of diabetic because it is casy to form the cross-linking agent with the biomacromolecule of protein, nucleic acid, lipide and so on, and then deposit in cells, interfere the normal functions of cell. The interactions of AGEs and RAGE, which lead to produce or activate of many cytokines of proinflammatory factor and profibrosis factor, and lead to the patho-changes of cell hypertrophia, base material accrementition and fibrosis of glomcrulus, take great effect on the generation and development of diabetic nephropathy and is one of the etiological factors. Therefore, intervention of the formation of AGES, elimination of the AGEs had formatted and amendment of the renal disease symptom induced by AGEs can prevent and cure the DN (Bohlender J M, Franke S, Stein G, et al. Advanced glycation end products and the kidney. Am J Physiol Renal Physiol, 2005, 289(4): 645-659).

Cortex Mori, the dry root cortex of *Morus alba* L., tastes sweet, frigidity and possesses the functions of removing heat from lung and relieving asthima, inducing diuresis to alleviate edema. Cortex Mori is usually used for dyspnea and cough due to lung-heat, oliguria due to dropsy and turg, puffiness of face muscle and skin. The recent pharmacology researches showed that the Cortex Mori possessed the activities of lowering blood sugar and blood pressure, diuresis, preventing cough and relieving asthima, anti-HIV, anti-tumor and so on. Since the active ingredients of 1-deoxynojirimycin and moran A for lowering blood sugar were isolated from Cortex Mori, more and more scholars are looking for new active ingredients of lowering blood sugar from Cortex Mori and next to improve a new drug for diabetic. DPMC is a new natural produce which is first time isolated from the extract of Cortex Mori and the synthetics produce of DPMC used only in chemical engineering field before is to prepare Diphenylmethane diisocyanate (MDI) which is the main material of polyurethane. Up till now, few of domestic or overseas literatures have been reported about the DPMC used in medical field.

SUMMARY OF THE INVENTION

It is an object of the invention to provide a pharmaceutical composition for diabetic nephropathy and its preparation, the active ingredient of the pharmaceutical composition is DPMC extracted from Cortex Mori.

To achieve the above object, the technical solution is as follows:

A pharmaceutical composition for diabetic nephropathy, the pharmaceutical composition is made up of DPMC and the conventional drug carrier; the active ingredient is in a percentage of 0.1-99.5% by weight.

Preferably, the active ingredient is in a percentage of 5-70% by weight.

The conventional drug carrier used in the pharmaceutical composition of the present invention is the conventional drug carrier of medical area. For example, the diluent and excipient is water; the filler is starch, sucrose, lactose and so on; the adhesive is cellulose derivate, alginate, gelatin or polyvinylpyrrolidone; the wetting agent is glycerine; the disintegrant is selected from agar, calcium carbonate or sodium bicarbonate; the absorption enhancer is quaternary ammonium compound; the surfactant is palmityl alcohol; the adsorption carrier is kaolin clay or soap clay; the lubricant is talc, calcium stearate, magnesium stearate or polyethylene glycol. In addition, other adjuvant such as flavor agent, sweetener can also be added to the composition.

By using normal methods of preparation, the pharmaceutical composition of the present invention can be prepared into normal dosage form which mainly is oral preparation, for example, the solid preparation is pellet, drug granules, pills, power, granulate, capsule, and the liquid preparation is aqua or oil suspending agent, elix and so on.

Preferably, the pharmaceutical composition is pellet, drug granules, pills or capsule.

The dosage of the pharmaceutical composition can be adjusted according the administer way and the severity degree of disease. Normally, the oral reference dosage of clinic is 20-120 mg/d.

It is a further object of the present invention to provide method for preparing the pharmaceutical composition of claim 1, comprising: mixing the 4,4'-diphenylmethane-bis (methyl) carbamates with the conventional drug carrier; preparing according the specific preparation process to obtain the pharmaceutical composition.

Preferably, the method of preparing the 4,4'-diphenylmethane-bis(methyl) carbamates is as follows:

A. Triturate the dry root cortex of Cortex Mori to power, add water and extract under reflux, combine the extract, concentrate to a certain volume under vacuum;

B. Add to the macroporous resin, elute with water, then with 95% EtOH, collect the elution of 95% EtOH and concentrate under vacuum;

C. Add to the silica gel and elute with petroleum, petroleum-acetic ether 100:1, petroleum-acetic ether 50:1, respectively, and a colorless lamellar crystal is attained from the elution of petroleum-acetic ether 50:1.

The pharmaceutical composition can be prepared according the normal preparation method in the pharmaceutical field. For example, mix the active ingredient and multi-carriers, then prepare into the dosage form as desired.

The present invention also provides the application of DPMC in preparing a pharmaceutical composition for diabetic nephropathy and its complications. Preferably, the application is the application of DPMC in preparing the pharmaceutical composition for diabetic nephropathy.

ADVANTAGES OF THE INVENTION

1 In this invention, DPMC is first time isolated from Cortex Mori and proved to possess the function of lowering the blood sugar, which indicate to provide the new drug for the patients of diabetic and complications of diabetic.

2 The pharmaceutical composition can be prepared into the oral dosage form such as drug granules, dripping pills, powder preparation for infusion, pellet and is convenient for use.

3 The pharmaceutical composition possesses noticeable effect on the prevention and cure for the damage of glomcrulus in diabetic. The pharmaceutical composition can remarkably prevent the rise of serum creatinine and lower the urinary volume, urine protein, and kidney index of rat in diabetic, which prove that the pharmaceutical composition takes a remarkable effect on the prevention and cure on diabetic nephropathy.

4 The pharmaceutical composition is obviously more effective than the water extract of Cortex Mori for diabetic nephropathy. In addition, because of the definite active ingredient and the easy control of quality, it can overcome the disadvantages of the traditional Chinese medicine in uncertainty of active ingredient, bad control of quality, many certain toxic side effects and so on.

BRIEF DESCRIPTION OF THE DRAWINGS

FIG. 1 shows the effect of DPMC on the express of TGFβ-1 of rat mesangial cells induced by AGEs (200×);

wherein A: normal control group; B: AGEs (5 mM/L); C: negative control group; D: water extract of Cortex Mon (0.1 mg/ml); E: DPMC (0.5 nM/L); F: DPMC (5 nM/L); G: DPMC (25 nM/L); H: DPMC (125 nM/L).

DETAILED DESCRIPTION OF THE PREFERRED EMBODIMENT

The present invention will be further explained in the embodiments hereinafter.

EXAMPLE 1

Preparation of DPMC

Triturate 10 kg dry root cortex of Cortex Mori to fine power, add 100 L water and extract under reflux for 2 hours thrice, combine the extract, concentrate to a certain volume under vacuum, add to the D101 macroporous resin, elute with water, then with 95% EtOH, collect the 95% EtOH elution and concentrate under vacuum, then add to the silica gel and elute with petroleum, petroleum-acetic ether 100:1, petroleum-acetic ether 50:1, respectively. A colorless lamellar crystal educes from the elution of petroleum-acetic ether 50:1. The structure was identified as 4 4'-diphenylmethane-bis(methyl) carbamates (DPMC) by infrared spectra, ultraviolet spectra, nuclear magnetic resonance and mass spectra. Molecular formula: $C_{17}H_{18}N_2O_4$; molecular weight: 314. The structure is shown as below:

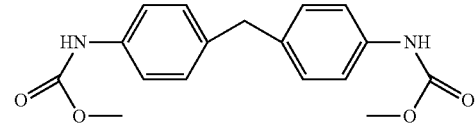

EXAMPLE 2

Pellet Pill Preparation of the Pharmaceutical Composition

The component per pill:

| | |
|---|---|
| DPMC | 12 mg |
| Lactose | 175 mg |
| Amylum maydis | 50 mg |
| Magnesium stearate | 3 mg |

Method of preparation: combine the DPMC, lactose and starch, moisten uniformly with water, sieve the combination and dry, sieve again, add Magnesium stearate, then crush the combination into tablet with 240 mg per pill and 12 mg active ingredient. The pellet pill takes a satisfactory effort on disease of high urine protein and diabetic nephropathy.

EXAMPLE 3

Capsule Preparation of the Pharmaceutical Composition

Steps:

A Take 4.2 g beeswax, add 125 g efamol, melt and mix under 80° C. water bath, allow to cool to the room temperature (25° C.), then add sufficient quantity of butylated hydroxyarisol, mix thoroughly;

B Add 0.25 g DPMC sieved with 100 mesh cribble and 5 g lecithin, add 250 g efamol, mix thoroughly as the core liquid of capsule, prepare to 1000 capsules.

The capsules prepared in the example take a satisfactory effect on hyperglycemia and diabetic nephropathy.

EXAMPLE 4

Drop Pill Preparation of the Pharmaceutical Composition

Recipe 15 g DPMC, triturate to fine power sieved with 200 mesh cribble, add to 15 g melted polyglycol 6000 base material, agitate thoroughly, prepare drop pills with dimethyl benzene silicon oil as the chiller, dry and finish the drop pill. The drop pill takes a satisfactory effort on the disease for increase of serum creatinine and decrease of urine creatinine, diabetic nephropathy.

EXAMPLE 5

Dispersible Tablet Preparation of the Pharmaceutical Composition

Weight accurately the quantity of a prescription dose: 280 g DPMC, 40 g lactose, 70 g cellulose microcrystallisate, 5.25 g polyvinylpolypyrrolid-one, 2.5 g aspartame, 6 g polyvidone and 4 g kalium vicarbonicum, misce bene the main medicine and the adjuvant by half-and-half increase, sieve with 80 mesh cribble for 2 times, put the combination to a proper container, add quantity sufficient of 15% (g/100 ml) polyethylene 6000 solved in 75% EtOH, prepare soft material and make the wet granules by crushing through the 20 mesh cribble, spread on the vitreous enamel plaque, dry under 70° C. for 2 hours in baking even of airblast, weigh accurately the dry granules, add 2.25 g the remaining polyvinylpolypyrrolidone and 1% (w/w) sodium dodecyl sulphate (SDS), mix uniformly, crush into 1000 pills with 4.7 mm round chop-out die, then make the 1000 dispersible tablets of DPMC. The dispersible tablet takes a satisfactory effort on diabetic nephropathy and its complications.

EXAMPLE 6

Pellet Pill Preparation of the Pharmaceutical Composition

| | |
|---|---|
| Active ingredient: | 70 g |
| Cellulose microcrystallisate: | 0.4 g |
| | Crush into 1000 pill |

Method of preparation: mix the active ingredient and cellulose microcrystallisate, prepare to soft material by moistening uniformly with water, make the combination into granules, sieve with 20 mesh cribble, dry under 80° C., sieve again, then crush into pills 70.4 mg per pill and 70 mg active ingredient per pill. The Pellet pill takes a satisfactory effort on diabetic nephropathy and its complications.

DPMC is used in the medicine field in this invention, and in order to prove the effect on diabetic nephropathy DPMC is applied to the experiments of effect on matrix accrementition of mesangial cells induced by AGEs and effect on pathological changes of STZ diabetic nephropathy model rat.

Experiment 1

Effect of DPMC on Matrix Accrementition of Mesangial Cells Induced by AGEs

The specific disease sign of diabetic nephropathy is the matrix indurascent of glomcrulus intercapillary cells induced by increase of extracellular matrix in mesangial region. Mesangial cell is the main component of glomcrulus mesenterium and takes an important role in sustaining the physiologic function of glomcrulus with many functions of contraction, endocrine secretion, division growth, immunity and phagocytosis. AGEs can induce the extracellular matrix accrementition of mesangial cells, which is the important pathological change of diabetic nephropathy.

1. Material and Agent

Rat messangial cell line HBZY-1 (Wuhan cell & biology institute); DPMC, water extract of Cortex Mori; bovine serum albumin, D-amylaceum (sigma company); Newborn Calf Serum (Sijiqing serum factory, Hangzhou); TGFβ-1 antibody (Canta Cruz); DAB coloration system (Gene Tech Biotechnology CompanyLimited); hydroxyproline content determination kit (Nanjing Jiancheng company).

2. Experimental Method 2.1 Preparation of Water Extract of Cortex Mori and AGEs

Preparation of Water Extract of Cortex Mori

Triturate quantity sufficient dry root cortex of Cortex Mori to power, add 10 time water and extract under reflux for 3 times, 2 hours per time, combine the extract, concentrate to a certain volume under vacuum for use.

Preparation of Water Extract of AGEs

Dissolved the 5% bovine serum albumin (BSA) without globulin and 0.5 mol/L D-amylaceum in 0.2 mol/L phosphate buffered solution (PBS, PH=7.2), filtrated with 0.24 μm micropore film and incubated under 37° C. for 60 days. After the incubation of the advanced glycation end products (AGEs) were finished, the umcombinated material was cleaned by extend dialyse method. Diluted to a necessary concentration and filtrated with 0.22 μm micropore film.

2.2 Mesangial Cells Culture and Staining

Concentration and time determination of AGEs which induce the pathological changes of mesangial cells:

Prepare of unicell suspension with HBZY-1 cells in log phase growth and DMEM medium with 5% newborn calf serum, take 100 μl/well (cell quantities: $1 \times 10^4$/well) to the 96-well plate, incubated under 5% $CO_2$ incubator at 37° C. for 24 hours, change with 100 μl the DMEM without serum and incubate another 24 hours to make the cells to anestrum (synchronization). Discard of the supernatant, add 90 μl DMEM medium with 5% newborn calf serum and 10 μl the different concentration of AGEs by gradient dilution with 6 repeat per group, incubate by gradient time, respectively, determinate the proliferation degree of rat mesangial cells by MTT. The result shows that 0.25 mg/ml AGEs and incubating for 48 h was the best condition for the experiment.

Put the coverslips pre-treated by poly-L-lysine into 24-well cell culture plates, in order to make the HBZY-1 cells grow on until synchronization. Discard of the supernatant, add 800 μl DMEM medium, 100 μl AGEs (final concentration is 0.25 mg/ml) in each medicine group, then add 100 μl water extract of Cortex Mori (final concentration is 0.1 g/L) or DPMC (final concentration is 0.5, 5, 25 or 125 nM/L). The normal control group is added 1 ml DEME medium when the AGEs group is added 900 μl DMEM medium and 100 μl AGEs (final concentration was 0.25 mg/ml). Every group repeats for 6 times. Then, all the groups are incubated under 5% $CO_2$ incubator at 37° C. for 48 h. Take suction of the cell supernatant for the content determination of hydroxyproline after the cells completely covered the coverslips and take out of the coverslips for immunocytochemistry staining.

Steps of TGFβ-1 staining: fix the coverslips covered by cells with 4% paraformaldehyde for 30 min, deactivate the endogenous horse radish peroxidase for 10 min with the 3% $H_2O_2$ solution of methanol prepared at that time, clean with distilled water for 3 times; block the non-specific antigen for 20 min with 5% BSA, add dropwise TGFβ-1 (1:500), remain under 4° C. for one night, wash for 2 min with PBS (PH 7.4)

for 3 times, add dropwise biotinylation antibody of goat anti mice, keep under 37 V for 30 min, wash for 2 min with PBS (PH 7.4) for 3 times, add dropwise avidin-bioepiderm-peroxydase complex labeled by HRP, keep under 37° C. for 30 min, wash for 5 min with PBS (PH 7.4) for 4 times, add dropwide 50 μl developer of DAB, color under room temperature for 15 min, clean uniformly with distilled water, stain lightly with hematoxylin again for 1 min, wash with water, dewater with alcohol, Permeabilizate with dimethyl benzene, cover the coverslip with neutro-gummi.

3 Statistical Analysis

Determinate the hydroxyproline content in cultured fluid of rat mesangial cells and express as $\bar{x}\pm s$, analyze by t-test; observe the TGFβ-1 expression in immunohistochemistry photo of rat mesangial cells under microscope.

4 Result

Effect of DPMC on Content Increase of Hydroxyproline in Supernatant of Rat Mesangial Cells Induced by AGEs As shown in Table 1, water extract of Cortex Mori and different doses of DPMC all can decrease the content increase of hydroxyproline in supernatant of rat mesangial cells induced by AGEs. Moreover, the large dose of DPMC (125 nM/L) performs best and is obviously better than the water extract of Cortex Mori.

TABLE 1

Effect of DPMC on content increase of hydroxyproline in supernatant of rat mesangial cells induced by AGEs

| group | Sample number | dose | hydroxyproline (μg/ml) |
|---|---|---|---|
| Normal control | 6 | — | 5.47 ± 1.23** |
| AGEs | 6 | — | 10.90 ± 8.03 |
| Extrs. of CM | 6 | 0.1 mg/ml | 7.54 ± 1.52* |
| DPMC | 6 | 0.5 nM/L | 7.68 ± 1.10* |
| DPMC | 6 | 5 nM/L | 7.76 ± 1.21* |
| DPMC | 6 | 25 nM/L | 5.71 ± 1.18* |
| DPMC | 6 | 125 nM/L | 4.76 ± 0.58**# |

Vs AGEs group,
*P < 0.05,
**P < 0.01,
Vs extract of CM,
P < 0.05

4.2 Effect of DPMC on the TGFβ-1 Expression of Rat Mesangial Cells Induced by AGEs As shown in FIG. 1, AGEs can make the TGFβ-1 expression of rat mesangial cells increase. The water extract of Cortex Mori and different doses of DPMC all can restrain the TGFβ-1 expression increase of rat mesangial cells. Moreover, the large dose of DPMC (125 nM/L) performs best and the different doses of DPMC are better than or equal to the water extract of Cortex Mori.

Experiment 2

Effect on Pathological Changes of STZ Diabetic Nephropathy Rat

1 Material and Reagent

Streptozotocin (Sigma); Wistar rat (offered by experimental animal center of southern medical university); B10BASE-PEARL separate automatic biochemistry analyzer (Shandong B10BASE Company).

2 Method of Experiment 2.1 Preparation of Water Extract of Cortex Mori

Triturate quantity sufficient dry root cortex of Cortex Mori to power, add 10 time water and extract under reflux for 3 times, 2 hours per time, combine the extract, concentrate to a certain volume under vacuum for use.

2.2 Administration

Model by administrating of low dose STZ for several times and determinate as the model rat of diabetic nephropathy, divide into 6 groups with 10 mice/group: model group, positive drug control group (aminoguanidine, 100 mg/kg), water extract of Cortex Mori group, 3 different concentration doses of DPMC group (high dose group: 4 mg/kg; middle dose group: 2 mg/kg; low dose: 1 mg/kg), normal control group.

Each group is given the same volume corresponding drug in different concentration or physiological saline everyday by intragastric administration for 14 weeks.

3 Statistical Analysis

Collect the 24 hour urine after administration is over, calculate the urine volume and determinate the content of total protein of urine, micro-albumen and urine creatinine; obtain blood by eye sockets and determinate the biochemical indicator with automatic biochemistry analyzer; take out of the double kidneys, fix with formalin and remain to histopathologic examination.

Statistical analysis of all determinations is calculated by interclass t-test and expressed as $\bar{x}\pm s$.

4 Result 4.1 Effect of DPMC on 24 Hour Urine Volume, Total Protein of Urine, Micro-Albumen and Urine Creatinine for Rat Model of Diabetic Nephropathy Induced by STZ As shown in Table 2, in model group, the 24 hours urine volume, eject volume of urine total protein and micro-albumen increase, and eject volume of creatinine in urine decrease obviously; nevertheless, the extract of Cortex Mori and the different doses all can restrain the changes above: decrease the 24 hour urine volume, lower the eduction volume of urine total protein and micro-albumen, increase the eduction volume of creatinine of diabetic nephropathy rat. Among these groups, the effect strengthens with the elevation of DPMC dose and the dose-effect relationship is obvious. Moreover, the effect of DPMC of large dose is obviously better than the water extract of Cortex Mori.

TABLE 2

Effect of DPMC on urine volume, total protein of urine, micro-albumen and urine creatinine of rat

| groups | Rat quantity | dose (mg/kg) | Urine V (24 hr, ml) | Total protein(mg) | micro-albumen (mg) | urine creatinine (mmol/L) |
|---|---|---|---|---|---|---|
| Normal control | 10 | — | 9.2 ± 1.5** | 18.5 ± 7.7** | 0.29 ± 0.07** | 12.4 ± 2.2** |
| Model | 10 | — | 65.6 ± 25.3 | 79.4 ± 29.2 | 1.63 ± 0.85 | 1.0 ± 0.3 |
| aminoguanidine | 10 | 100 | 36.2 ± 21.7* | 43.2 ± 29.9* | 1.00 ± 0.27* | 4.0 ± 2.3** |

TABLE 2-continued

Effect of DPMC on urine volume, total protein of urine, micro-albumen and urine creatinine of rat

| groups | Rat quantity | dose (mg/kg) | Urine V (24 hr, ml) | Total protein(mg) | micro-albumen (mg) | urine creatinine (mmol/L) |
|---|---|---|---|---|---|---|
| Extra. of CM | 10 | 2000 | 39.5 ± 18.3* | 56.1 ± 25.2* | 1.59 ± 0.63 | 2.1 ± 0.9* |
| DPMC | 10 | 1 | 59.9 ± 21.8 | 69.1 ± 20.4 | 1.57 ± 0.56 | 1.4 ± 0.6 |
|  | 10 | 2 | 41.3 ± 16.4* | 54.0 ± 17.4* | 0.93 ± 0.55*# | 2.9 ± 1.2** |
|  | 10 | 4 | 33.9 ± 22.2* | 46.2 ± 21.6*# | 0.92 ± 0.42*# | 4.3 ± 2.0**# |

($\bar{x} \pm s$, n = 10)
Vs model group,
*P < 0.05,
**P < 0.01,
Vs extract of CM,
P < 0.05
P < 0.01

4.2 Effect of DPMC on Scrum Biochemical Indicator for Rat of Diabetic Nephropathy As shown in Table 3, extract of Cortex Mori and different dose of DPMC all can decrease the lever of serum total cholesterol (TC), malonaldehyde (MDA), serum creatinine (SC), blood urea nitrogen (BUN), AGEs and low-density lipoprotein (LDL), elevate the lever of serum superoxide dismutase (SOD) for diabetic nephropathy rat. With the elevation of dose, the effect of DPMC strengthen, moreover, the effect of all the concentration of DPMC are better than or equal to the water extract of Cortex Mori.

TABLE 3

Effect of DPMC on serum biochemical indicator for rat of diabetic nephropathy

| groups | Dose (mg/kg) | TG (mmol/L) | SOD (U/ml) | MDA (nmol/L) | SC (umol/L) | BUN (mmol/L) | AGEs | LDL (mmol/L) |
|---|---|---|---|---|---|---|---|---|
| Normal control | — | 1.89 ± 0.22** | 525 ± 26** | 4.4 ± 0.7** | 71.7 ± 19.2** | 6.5 ± 0.7** | 264 ± 53** | 0.78 ± 0.30** |
| Model | — | 3.36 ± 0.72 | 481 ± 25 | 9.3 ± 2.6 | 96.3 ± 13.4 | 7.9 ± 1.3 | 351 ± 59 | 2.12 ± 0.67 |
| Amino-guanidine | 100 | 3.35 ± 0.87 | 516 ± 20** | 5.9 ± 1.7** | 77.7 ± 20.3* | 6.6 ± 0.8* | 283 ± 78* | 2.01 ± 0.58 |
| Extr. of CM | 2000 | 2.68 ± 0.86* | 510 ± 44* | 6.8 ± 2.4* | 79.3 ± 24.7* | 6.8 ± 1.3* | 291 ± 52 | 1.66 ± 0.54* |
| DPMC | 1 | 3.23 ± 0.76 | 498 ± 33 | 7.8 ± 2.3 | 91.0 ± 31.1 | 7.0 ± 1.0 | 290 ± 59 | 1.91 ± 0.55 |
| DPMC | 2 | 2.76 ± 0.80* | 513 ± 41* | 6.8 ± 1.9* | 76.6 ± 24.5* | 6.6 ± 1.2* | 289 ± 56* | 1.51 ± 0.53* |
| DPMC | 4 | 2.57 ± 0.80* | 520 ± 29** | 6.8 ± 1.3* | 74.0 ± 17.1** | 6.5 ± 1.5** | 281 ± 78* | 1.43 ± 0.36* |

($\bar{x} \pm s$, n = 10)
Vs model group,
*P < 0.05,
**P < 0.01

4.3 Effect of DPMC on the CTGF Expression and Pathohistology of Rat Glomcrulus in Model of Diabetic Nephropathy As shown in Table 4, compared with the normal control group, the glomcrulus CTGF expression in model of diabetic nephropathy increase (P<0.01) and the damage of patho-tissue also increase; the water extract of Cortex Mori and DPMC of different doses all can decrease the glomcrulus CTGF expression of rat in model of diabetic nephropathy induced by STZ, degrade the pathology score of damage. With the elevation dose, the effect of DPMC strengthen, moreover, the effect of all the concentration of DPMC are better than or equal to the water extract of Cortex Mori.

TABLE 4

Effect of DPMC on the CTGF expression and pathohistology of rat glomcrulus in model of diabetic nephropathy
($\bar{x} \pm s$, n = 10)

| Groups | Rat quantity | dose (mg/kg) | CTGF(%) | Pathology score |
|---|---|---|---|---|
| Normal control | 10 | — | 4.6 ± 1.8** | 0.3 ± 0.5** |
| model | 10 | — | 9.5 ± 3.2 | 3.4 ± 1.3 |
| Aminoguanidine | 10 | 100 | 5.9 ± 2.2* | 2.1 ± 1.0* |
| Extra. of CM | 10 | 2000 | 6.5 ± 2.9* | 2.2 ± 0.9* |
| DPMC | 10 | 1 | 7.1 ± 1.6* | 2.7 ± 1.0 |

TABLE 4-continued

Effect of DPMC on the CTGF expression and pathohistology of rat glomcrulus in model of diabetic nephropathy
($\bar{x} \pm s$, n = 10)

| Groups | Rat quantity | dose (mg/kg) | CTGF(%) | Pathology score |
|---|---|---|---|---|
| DPMC | 10 | 2 | 6.4 ± 2.7* | 1.8 ± 1.3* |
| DPMC | 10 | 4 | 6.0 ± 3.1* | 1.2 ± 1.1**# |

Vs model group,
*P < 0.05,
**P < 0.01;
vs Extract of MC,
p < 0.05

What is claimed is:

1. A method for treating diabetic nephropathy in a subject comprising the steps of:
   a). providing a pharmaceutical composition consisting of 4, 4'-diphenylmethane-bis(methyl) carbamates (DPMC) and at least one pharmaceutically acceptable drug carrier, wherein the 4, 4'-diphenylmethane-bis(methyl) carbamates (DPMC) is in a percentage of 0.1-99.5% by weight of the pharmaceutical composition, and
   the pharmaceutical composition is administered in a clinical dosage form selected from the group consisting of:
   (1) a pellet pill consisting of 4, 4'-diphenylmethane-bis(methyl) carbamates (DPMC), lactose, Amylum maydis, and magnesium stearate, and
   (2) a drop pill consisting of 4, 4'-diphenylmethane-bis(methyl) carbamates (DPMC), polyglycol 6000, and dimethyl benzene silicon oil, and
   (b). administering an effective amount of the pharmaceutical composition in a clinical dosage form to a patient in need thereof, wherein the effective amount of 4, 4'-diphenylmethane-bis (methyl) carbamates (DPMC) is 20-120 mg per day.

2. The method of claim 1, wherein the 4, 4'-diphenylmethane-bis(methyl) carbamates (DPMC) is in a percentage of 5-70% by weight of the pharmaceutical composition.

* * * * *